United States Patent [19]

Chappell et al.

[11] Patent Number: 5,384,244
[45] Date of Patent: Jan. 24, 1995

[54] DETECTION OF SCHISTOSOMIASIS ANTIBODIES

[76] Inventors: Cynthia L. Chappell, 4337 Betty St., Bellaire, Tex. 77401; Marc H. Dresden, deceased, late of Houston, Tex. by Judith H. Dresden, legal representative, 3610 Underwood, Houston, Tex. 77025

[21] Appl. No.: 960,121

[22] Filed: Oct. 13, 1992

Related U.S. Application Data

[63] Continuation-in-part of Ser. No. 447,799, Dec. 8, 1989, abandoned.

[51] Int. Cl.$^6$ ............................................. G01N 33/569
[52] U.S. Cl. ............................... 435/7.22; 435/7.92; 435/7.94; 435/970; 436/531; 436/811
[58] Field of Search .................... 435/7.22, 7.4, 7.94, 435/23, 447; 436/531, 534; 530/328

[56] References Cited

U.S. PATENT DOCUMENTS 3,770,383 11/1973 Price ........................... 436/531
4,554,101 11/1985 Hopp et al. ..................... 514/13

OTHER PUBLICATIONS

Chappell et al., "Cloned *Schistosoma mansoni* Proteinase (Hemoglobinase) as a Putative Sevodiagnostic Reagent", J. Clin. Microbiol., 27(1):196–198 (Jan. 1989).
Davis et al. "Cloning and Gene Expression of *Schistosoma mansoni*: Protease", J. Biol. Chem., 262(26):12851–12855 (Sep. 15, 1987).
Voller et al. "Enzyme-Linked Immunosorbent Assay" in Manual of Clinical Laboratory Immunology, pp. 99–109 (1986). American Society for Microbiology (Washington D.C.).
Hopp et al. "A Computer Program for Predicting Protein Antigenic Determinants", Molecular Immunology, 20(4):483–489 (1983).
Bangs, Uniform Latex Particles, Seradyn, Inc. (Indianapolis, Ind.), pp. 11–16 (1984).
Klinkert et al. "Expression of diagnostic 31/32 Kilodalton proteins of *Schistosoma mansoni* as fusions with bacteriophaga MS2 polymerase", Mol. Biochem. Parasit., 27(2–3):233–240 (Jan. 15, 1988).
Klinkert et al. "Primary structures of Sm 31/32 diagnostic proteins of *Schistosoma mansoni* and their identification as proteases", Mol. Biochem. Parasit., 33(2):113–122 (Mar. 1, 1989).

*Primary Examiner*—Carol E. Bidwell
*Attorney, Agent, or Firm*—Gunn & Kuffner

[57] ABSTRACT

The present disclosure is directed to a peptide having active binding sites in a protein wherein the binding sites attract and hold antibodies for schistosomiasis in humans. A test reagent is set forth. Separate binding sites in the complex protein have been identified, and the binding sites in such reagent define the mechanism whereby the antibodies in the human serum provide a test reaction.

9 Claims, 2 Drawing Sheets

```
 89        I           II   112   225    III       237
T F L|K V L K G D K S|A G G|K V L K S G K N D|D.//..D Q|Q Y K E V K R E T|D
```

▨▨▨▨▨▨▨▨▨▨▨▨▨▨▨▨▨▨ SMP 22

▨▨▨▨▨▨▨▨▨▨▨▨ SMP 11

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Lys  Val  Leu  Lys  Ser  Gly  Lys  Asn  Asp
 1                       5
```

( 2 ) INFORMATION FOR SEQ ID NO:2:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( v ) FRAGMENT TYPE: internal fragment ( x ) PUBLICATION INFORMATION:
        ( A ) AUTHORS: Davis, A.H.
        ( B ) TITLE: Cloning and Gene Expression of Schistosoma Mansoni Proteinase
        ( C ) JOURNAL: J. Biol. Chem.
        ( D ) VOLUME: 262
        ( F ) PAGES: 12851-855
        ( G ) DATE: 1987
        ( K ) RELEVANT RESIDUES IN SEQ ID NO:2: FROM 89 TO 112

( x i ) SEQUENCE DESCRIPTION: SEQ ID NO:2:

```
Thr  Phe  Leu  Lys  Val  Leu  Lys  Gly  Asp  Lys  Ser  Ala
 90                       95                      100

Gly  Gly  Lys  Val  Leu  Lys  Ser  Gly  Lys  Asn  Asp  Asp
              105                      110
```

( 2 ) INFORMATION FOR SEQ ID NO:3:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( v ) FRAGMENT TYPE: c-terminal fragment ( x ) PUBLICATION INFORMATION:
        ( A ) AUTHORS: Davis, A.H.
        ( B ) TITLE: Cloning and Gene Expression of Schistosoma Mansoni Proteinase
        ( C ) JOURNAL: J. Biol. Chem.
        ( D ) VOLUME: 262

(F) PAGES: 12851-855
(G) DATE: 1987
(K) RELEVANT RESIDUES IN SEQ ID NO:2: FROM 89 TO 112

(xi) SEQUENCE DESCRIPTION: SEQ ID NO:3:

Asp Gln Gln Tyr Lys Glu Val Lys Arg Glu Thr Asp
230              235              240

DETECTION OF SCHISTOSOMIASIS ANTIBODIES

This application is a continuation-in-part of copending application Ser. No. 447,799, filed on Dec. 8, 1989 now abandoned. The United States government may own certain rights in this and the patent application.

BACKGROUND OF THE DISCLOSURE

The present disclosure is directed to isolated peptides useful in the testing of and diagnosis of infection by the human parasite of the genus Schistosoma and to methods of testing employing such peptides.

The world distribution of schistosomiasis is typically endemic in tropical zones wherein the schistosome's life cycle is dependent on known, regionally specific intermediate snail hosts. See, *Hunter's Tropical Medicine*, Sixth Edition, W.D. Saunders Company, pages 713 et seq. The epidemiology of schistosomiasis typically involves geographic regions between 36° north and 34° south latitude and further characterized by having fresh water temperatures in the range of about 25°–30° C. The endemic populations include people of all ages, but the disease particularly seems to attack young boys, ages 5 to 10. The infection mechanism involves mere contact with the water of the region assuming the appropriate snail population. Other details regarding the pathology of the disease are set forth in representative sources such as the text mentioned above. Suffice it to say, it is a debilitating parasitic disease.

Present day techniques of detection of the disease in the human host primarily involve identification of the schistosome egg. There are multiple techniques available, but they primarily involve microscopic examination of human feces, and such tests are set forth in the referenced text. Prior art serologic tests have tended to be somewhat insensitive and somewhat lacking in specificity. Most serologic tests that have been developed can provide positive indication of the disease only exceedingly late after the onset of infection. By contrast, the test of the present disclosure will detect the antibody before or prior to egg production by the parasite worm in the human host.

As can be understood, the chronic symptoms of schistosome infestation are more severe than the subtle symptoms occurring prior to egg production. Thus, prior art test responses (sensitivity and specificity) are variable because impure schistosomal antigens are used. Contrary to this problem, the peptides of the present disclosure can be synthesized in substantial purity and consistency and, in that sense, represent the ultimate in available test reagents. Testing can now be carried out with a minimum of specialized laboratory equipment, even in ill-equipped field conditions in an endemic population. Thus, the peptides can be employed in testing large population groups or a single individual, and these tests can be carried out, even in the most adverse of circumstances.

BRIEF DESCRIPTION OF THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

FIG. 1A shows hydrophilicity analysis of the *S. mansoni* cysteine proteinase, CP1. The three probable antigenic sites (I, II, and III) are indicated by the solid bars. FIG. 1B shows, the primary sequence of each site is indicated by open boxes. Synthetic peptide sequences SMP 22 and SMP 11 are shown by hatched boxes in FIG. 1B.

FIGS. 2A and 2B show antibody response (IgG) in the sera of uninfected (light stipple) or *S. mansoni* - infected (dark stipple) mice (FIG. 2A) and humans (FIG. 2B) to CP1 derived synthetic peptides. Equimolar concentrations of peptides were covalently linked to microtiter wells. Each value is the mean of at least 3 separate wells. Each value is the mean of at least 3 separate determinations; standard deviations are indicated by error bars. Statistical comparisons were evaluated by student's t test (unpaired).

FIGS. 3A and 3B show the results of a competition ELISA assay using intact CP1 bound to microtiter wells. *S. mansoni* - infected mouse (FIG. 3A) or human (FIG. 3B) sera (solid line) were pre-incubated overnight at 4C. with SMP 22 (dotted, dashed line) or SMP 12 (dotted line). Control sera are indicated (dashed line). Each value is the mean of three separate experiments; standard deviation for each dilution is indicated by error bars.

DETAILED DESCRIPTION OF THE PREFERRED EMBODIMENT

The schistosoma parasite proteinase CP1 has been previously isolated, purified and characterized. See Davis, A.H., et al. *Cloning and Gene Expression of Schistosoma Mansoni Proteinase.* J. Biol. Chem. 262:12851–855 (1987). This protein, characterized further as a 1-Galactosidase fusion protein, has been determined to provide a strongly specific and sensitive immune response indicative of the presence of schistosomiasis infection, whether that infection be by *S. mansoni* or either of the other two schistosoma species known to cause this disease, namely *S. japonicum* and *S. haematobium*.

As a generalization, laboratory animals (preferably mice) can be infected with the schistosome parasite which results in an acute infection typically after about two months of maturation. The parasites are collected from the mice and the CP1 protein is ultimately isolated from the worms. This represents about one part in one thousand of the total protein captured. The native protein can be used as a test reagent, but that is usually difficult to accomplish, primarily because of two reasons. For one, it is a fairly large protein. Moreover, it is a protein which is difficult to isolate and provide in a relatively pure state. By contrast, it is possible to clone the CP1 protein. Its description is set forth by Alan Davis as noted above. Through this, the recombinant product can be provided.

Figure 1A:
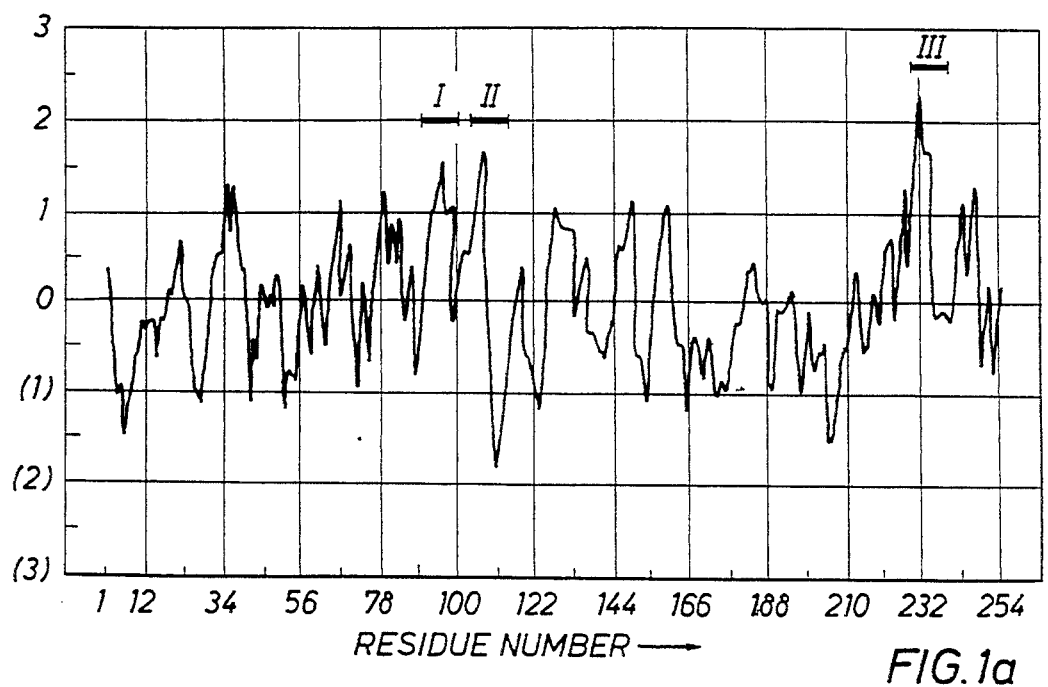
FIGS. 1A, 1B, 2A, 2B, 3A and 3B are VARIED graphs which describe for comparative purposes the peptide test reagent set forth in the present disclosure.
Figure 1B:
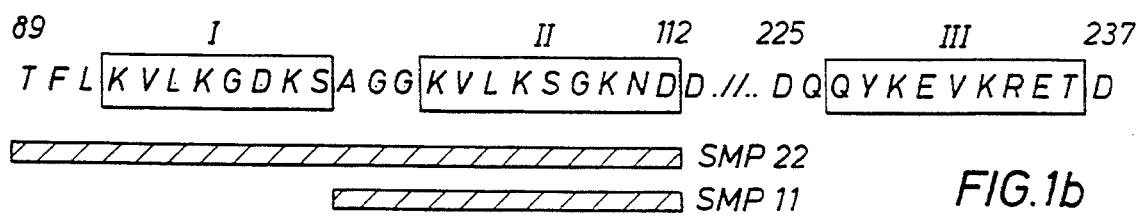

The *Schistosoma mansoni* cysteine proteinase CP1 has been subjected to hydrophilic analysis. FIG. 1A attached hereto sets forth this analysis where the abscissa is the residue number and the ordinate indicates relative site activity. As shown in FIG. 1A, three sites are suggested, and it will be observed that Sites I and II are quite similar. Two synthetic peptides, SMP 11 and SMP 22, shown in FIG. 1B can be synthesized using the data in FIG. 1A where the Sites I, II and II are represented by boxes in both FIGS. 1A and 1B; It will be noted in particular that the larger of the peptides involves the full range of the residue numbers from 89 to 111, a range of 23; the smaller of the synthetic peptides involves twelve, and both appear to have the antibody binding propensity verified by test procedures.

Inspection of FIG. 1A will show that the hydrophilic analysis of the protein CP1 over the full length sequence of that proteinase clone supports the three sites designated in FIG. 1A. The primary sequence at the sites carries a strong suggestion that these areas involve repeat epitopes. The peptides involving Sites I and II or Site II only are thus designated as SMP 22, and SMP 11 respectively. Synthesis of these and testing for antibody binding activity has verified the test reagent success.

Analysis of the CP1 protein primary sequence has determined three peak hydrophilic areas which are identified in FIG. 1A as Sites I, II and III. Synthetic peptides encompassing Sites I and II (jointly) or Site II alone have shown an ability to bind antibodies specific to schistosomiasis infection. Moreover, they complete with the binding of polycolonal antibodies to the whole protein CP1. Applicants have determined that synthetic peptides containing the sequence Lys Val Leu Lys Ser Gly Lys Asn Asp (SEQ ID NO: 1) comprise an immunodominant epitope of the protein molecule CP1. Test verification using an ELISA assay system has distinguished sera from schistosome infected humans, and a contrast from those not infected has been confirmed. In other words, a schistosome infected human has a distinctive antibody which responds to the test while those who are not infected do not so respond.

Figure 2A:
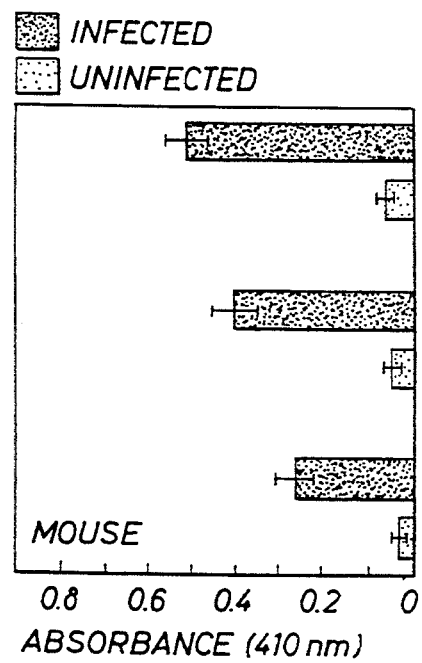
Figure 2B:
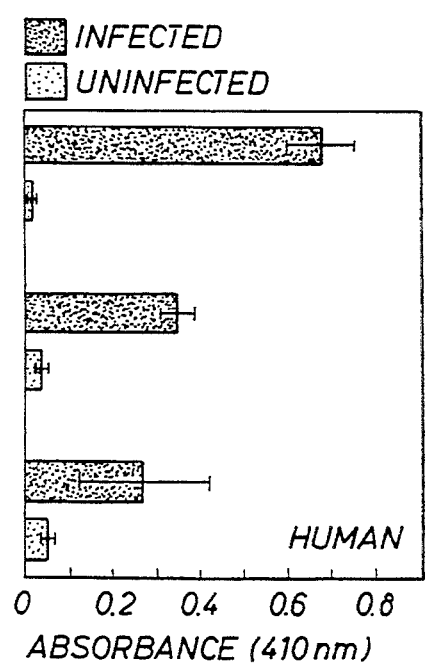

One such test which verifies the success of both peptides SMP 11 and SMP 22 shows a covalent linking mechanism to humans (or mice for that matter). In this test, a control peptide formed of a randomly scrambled version of SMP 11, was also employed and the results compared to those obtained with the SMP 11 and SMP 22. In all instances, sera from infected mice and humans provided significantly higher absorbance in contrast with the controlled sera. FIGS. 2A and 2B of the drawings illustrates this contrast with human and mouse response to the three peptides.

As will be observed, FIGS. 2A and 2B show the sera of uninfected mice or humans in contrast with *Schistosoma mansoni* infected mice and humans. In all tests, the peptide was tested with equimolar concentrations of peptides which are covalently linked to microtiter wells. Multiple tests were used to provide the data of FIGS. 2A and 2B, and the standard deviations are indicated by the error bars imposed thereon. FIG. 2 shows that sera from infected mice produced greater binding by both SMP 11 and SMP 22. It appears further that SMP 22 can bind significantly more antibody than SMP 11. Results from infected human sera are similar. However, the scrambled peptide bound the antibody to the same degree as did other unrelated peptides which may indicate polyclonal activation of the plasma cells.

Figure 3A:
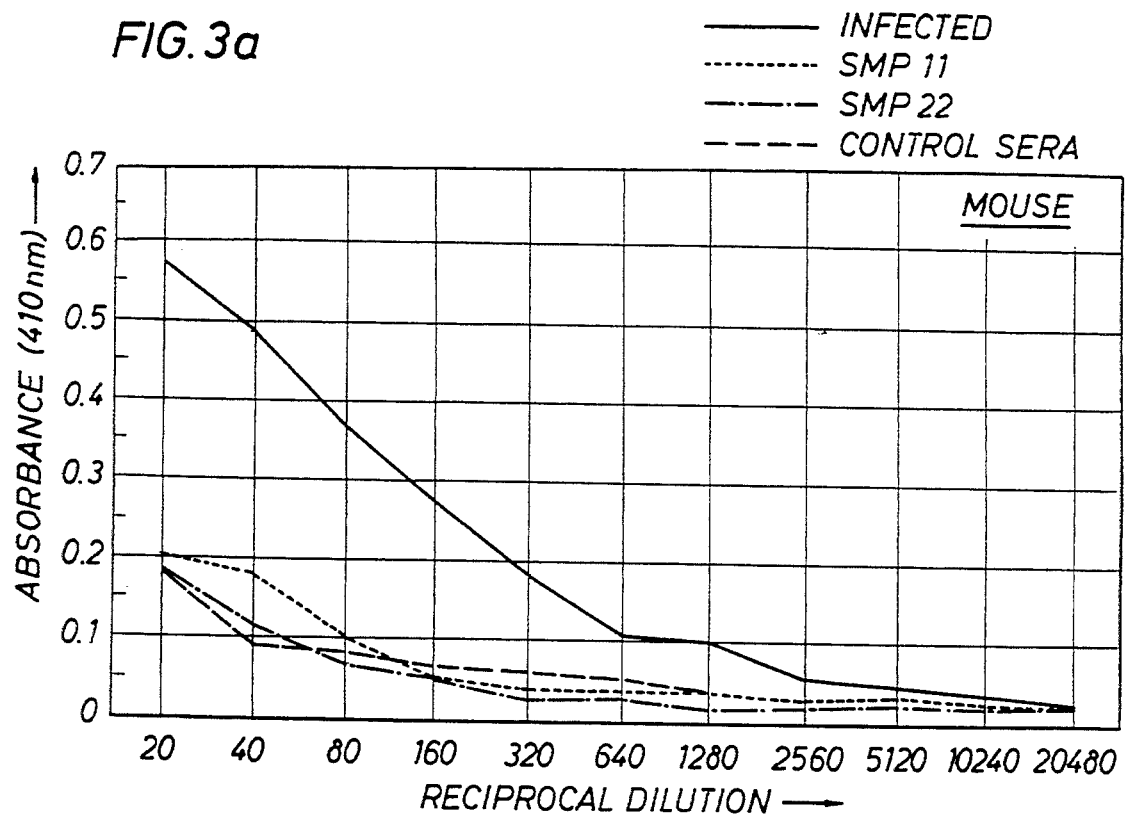
Figure 3B:
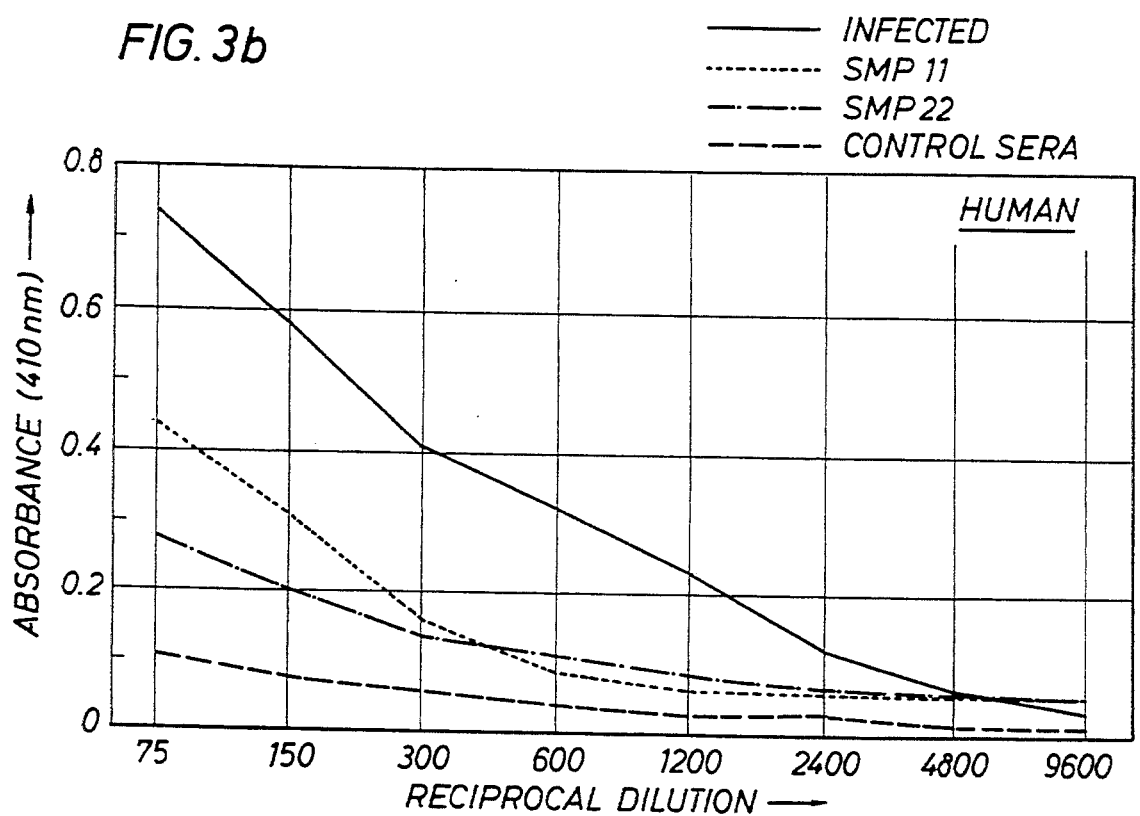

FIGS. 3A and 3B show dilution curves for antibody binding of controlled sera, infected sera only, and infected sera pre-incubated with peptides. The dilution should be noted first; the first dilution is typically in the ratio of 1:20. Subsequent dilutions by two are implemented to have ratios of 1:40, 1:80, 1:160, etc. as shown in the abscissa of FIGS. 3A and 3B. A green light (wave length of 410 nanometers) is used for the absorbence test. In the mouse, both peptides (SMP 11 and also SMP 22) were effective inhibitors of antibody binding to the intact CP1 protein molecule even at quite high serum concentrations. SMP 22 showed slightly more inhibitory activity compared with the SMP 11 peptide. Both peptides completely inhibited binding at a serum dilution of 1:80, see FIG. 3A. By contrast, antibodies from human infection were partially inhibited at higher serum concentrations and did not reach complete inhibitions until sera was diluted to about 1:640. This data suggests that SMP 22 inhibited better than SMP 11.

The conclusion derived from the foregoing data is that the single epitope (SMP 11) is capable of inhibiting polyclonal antibody binding to the protein CP1. This may indicate the existence of a single epitope, or likely also suggests two or three cross-reactive epitopes. The differences in the degree of inhibition between mice and humans probably derive from the differences in the infection, namely, that the mice are acutely infected while the human sera is from those who are only chronically infected.

Detection of protein CP1 immune complex in human sera, coupled with high titer verification, enables a number of desirable testing procedures. The microtiter process involves the addition of a second antibody and subsequent absorbance testing at a specified light frequency, and yields a measure of light transmission. This in turn yields both a qualitative and quantitative result; that is, the subject's blood is either infected or not, and a relative measure of infection is indicated in accordance with known techniques involving microtiter testing.

However, while the microtiter test procedure is well known and can be carried out in a well equipped laboratory, it is not always available. In remote endemic populations, as an alternative to the microtiter testing procedure set forth above, advantage can be taken of the ELISA or LATEX AGGLUTINATION assays. In these procedures, the isolated peptide (either SMP 11 or SMP 22 or both) can be linked to an inert substrate and it will subsequently bind to antibodies from patient blood.

In a typical agglutination assay, polystyrene beads which are a few microns in diameter, commonly more than ten microns in diameter up to perhaps one hundred or two hundred microns in diameter, are coated with the isolated peptide of the present disclosure by means of a suitable solvent removed by evaporation and then distributed evenly on the test surface. This yields an exposed set of polystyrene beads of appropriate size having receptor sites defined by the peptide coating. When the infected patient's blood serum is applied to this test surface, there will be an aggregation (i.e., clumping) of the beads.

Suitable test devices employing the latex agglutination assay process may be devised from paper or cardboard in the form of a slide coated with polystyrene beads supported on a carrier which is typically a black glossy waxed paper. Where there are no antibodies, i.e., when the patient is not infected, the clumping does not occur. Clumping occurs by the linking of the antibody from the patient's serum. This can be visually recognized and is a test which can be carried out to provide simple, straightforward and quickly determined infection measurement.

This test utilizing the supportive substrate described above with the carrier beads (subject to agglutination on positive testing) is therefore the kind of test procedure which can be carried out in remote conditions absent electrical power for operation of test equipment, and does not require highly trained test personnel to execute the test reliably. In other words, a low cost, inexpensive field use test is provided thereby.

The test procedure of this invention is specific and particularly suitable for the *Schistosoma mansoni* species, but will also be specific for and is therefore highly useful with the two other schistosome species that commonly infect humans. It is not cross-reactive to other blood serum antibodies that are typically encountered in the endemic populations (malaria being one example) or to infections from other closely related trematodes, such as *F. hepatica* or *C. sinensis*. Through the use of the present test, a positive and specific indication for the schistosomiasis infection is thus provided so that treatment can proceed promptly thereafter.

---

What is claimed is:

1. A test procedure for determining the presence of schistosomiasis antibodies in a blood sample comprising the steps of applying serum from said sample to a supportive substrate having immobilized thereon a synthetic peptide reagent selected from the group consisting of SMP 11 and SMP 22 or combinations thereof containing sequence Lys Val Leu Lys Ser Gly Lys Asn Asp (SEQ ID NO:1) and detecting specific binding of the schistosomiasis antibodies with the reagent after appropriate incubation time to determine the presence or absence of schistosomiasis antibodies.

2. The method of claim 1 wherein the supportive substrate is a microtiter well, and detecting specific binding includes the steps of adding a labelled antibody which specifically binds to the schistosomiasis antibodies and irradiating the well with light of a specified wave length to determine the presence of the label specifically bound to the well.

3. The method of claim 1 wherein the synthetic peptide reagent is SMP 11.

4. The method of claim 1 wherein the synthetic peptide reagent is SMP 22.

5. The method of claim 1 wherein the supportive substrate having the synthetic peptide reagent immobilized thereon is in the form of plastic beads present on a test surface, the method further comprising applying the serum to the test surface to cause the beads to become suspended in the serum and detecting specific binding by visually determining agglutination of the beads.

6. The method of claim 1 wherein the supportive substrate is in the form of plastic beads distributed on a paper base with a waxed surface.

7. A method for testing for schistosomiasis antibodies in a human wherein the method comprises the steps of:
 (a) immobilizing a synthetic peptide reagent selected from the group consisting of SMP 11 and SMP 22 or combinations thereof containing sequence Lys Val Leu Lys Ser Gly Lys Asn Asp (SEQ ID NO:1) on a supportive substrate;
 (b) obtaining serum from blood collected from the human for testing;
 (c) applying the serum to the supportive substrate under conditions suitable to cause a measurable specific binding reaction to take place between schistosomiasis antibodies present in the serum and the synthetic peptide reagent; and
 (d) determining the presence of the measurable specific binding reaction.

8. The method of claim 7 wherein the synthetic peptide reagent is SMP 11.

9. The method of claim 7 wherein the synthetic peptide reagent is SMP 22.

* * * * *